Figure 1:
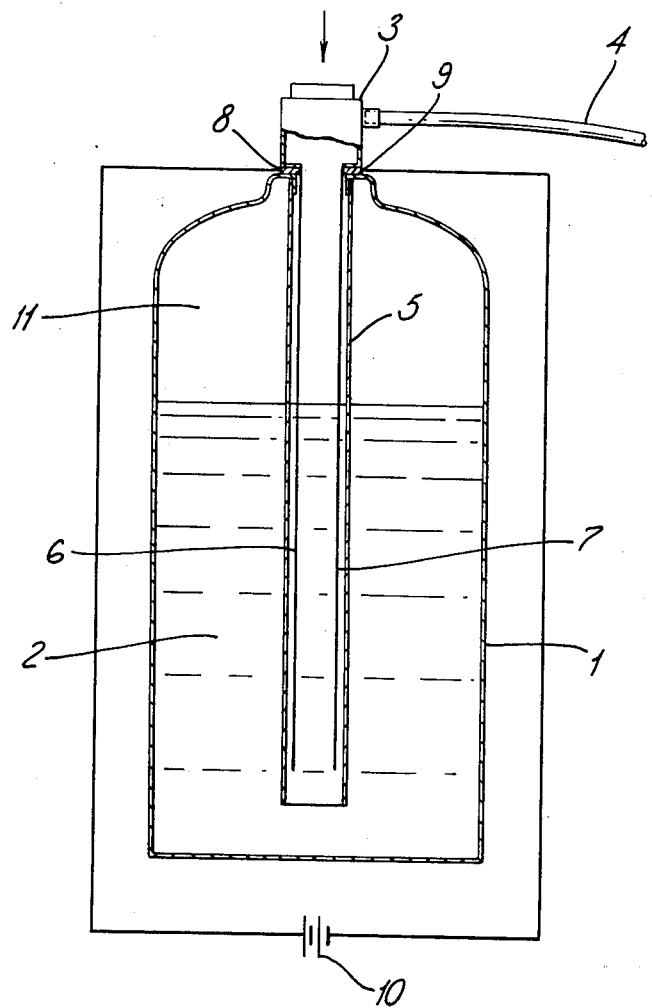

United States Patent [19]

Rasmussen

[11] 3,996,126
[45] Dec. 7, 1976

[54] MEANS FOR REMOVAL OF ADSORBED FILM AND MICROORGANISMS FROM TEETH AND ORAL CAVITIES

[76] Inventor: Oystein E. Rasmussen, Hosleveien 119, 1340 Bekkestua, Norway

[22] Filed: Oct. 31, 1974

[21] Appl. No.: 519,659

[30] Foreign Application Priority Data
Nov. 28, 1973 Norway .............. 4307/73

[52] U.S. Cl. ............. 204/271; 204/149; 204/278; 424/45
[51] Int. Cl.² ......... C25B 1/26; C25B 9/00
[58] Field of Search ............ 424/45; 204/278, 275, 204/271, 270, 149

[56] References Cited
UNITED STATES PATENTS

| | | | |
|---|---|---|---|
| 308,276 | 11/1884 | Paine | 204/278 X |
| 1,401,035 | 12/1921 | Boisen | 204/278 |
| 3,544,442 | 12/1970 | Anderson | 204/275 |

*Primary Examiner*—John H. Mack
*Assistant Examiner*—A. C. Prescott
*Attorney, Agent, or Firm*—Cushman, Darby & Cushman

[57] ABSTRACT

A method and means whereby a neutral salt water solution is electrolyzed in a confined compartment to achieve decomposition products which remove adsorbed film and microorganisms from teeth and oral cavity. The decomposition solution is sprayed from a container whereby the compartment is arranged in connection with the spray means. The electrodes in the compartment are activated from a current source.

9 Claims, 2 Drawing Figures

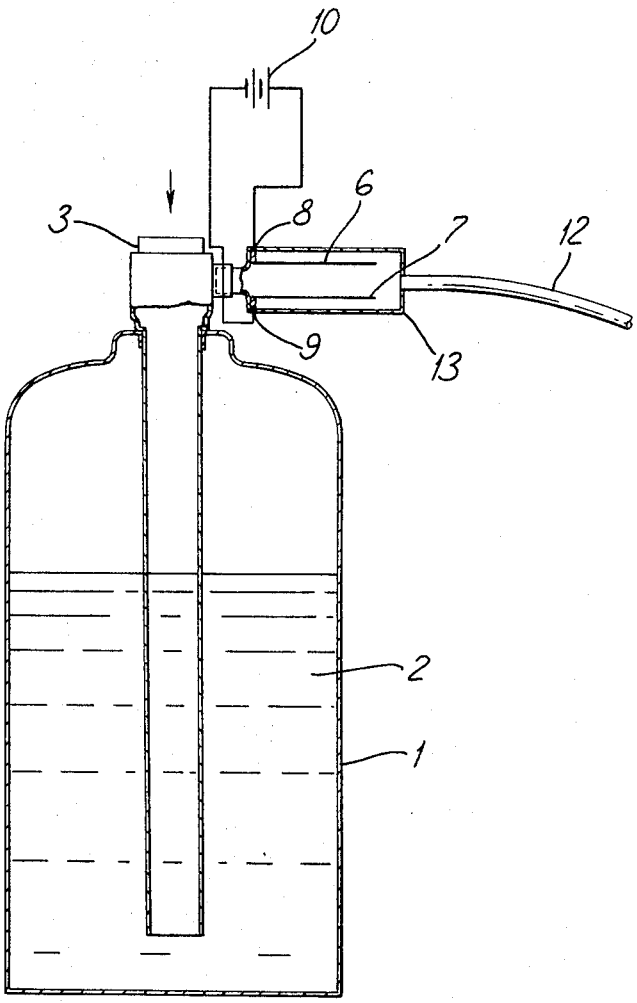

MEANS FOR REMOVAL OF ADSORBED FILM AND MICROORGANISMS FROM TEETH AND ORAL CAVITIES

The present invention relates to a method and means for treating teeth and oral cavities.

In recent years, the fact that the conventional methods of cleaning teeth are neither adequate nor satisfactory has become more and more widely acknowledged. A toothpaste having abrasive properties and chemical additives is most frequently used for cleaning teeth, and the film on the teeth can, to some extent, be removed where accessible; however, by such brushing, and particularly together with an abrasive, the effect on the dental enamel with constant use over a long period of time is apt to cause damage. The additives in toothpaste for removal of dental film are not entirely satisfactory, moreover, and can have some negative effects.

A certain disinfection of the oral cavity can be achieved by rinsing the oral cavity and teeth with a disinfectant, but this procedure does not efficiently remove the adsorbed molecular film.

The object of the present invention is therefore to provide a novel method and means for treating teeth which removes adsorbed dental film and microorganisms to a substantially improved degree, and, at the same time, allows access to all parts of the teeth and the oral cavitiy, whereby unnecessary wear of the dental enamel is avoided and the substances used have no adverse effects on the oral tissue.

The invention resides in the teaching that the film formed on the teeth and in the oral cavity consists of a primary film built up substantially from glycoproteins and muco-polysaccharides. The said primary film provides a fertile base for bacteria and the like present in the oral cavity and, from this starting point, causes the formation of mineralized calculus, caries, tissue inflamation and periodontal disease. At the gingival margin, the said primary film is the basis of bacterial attack, which may lead to gingivitis and, in particularly unfortunate circumstances, to infections which spread along the jaw and may entail serious side effects.

The object of the invention is thus to remove the said primary film in a simple and careful manner with no effect on the physiological conditions in the oral cavity, such that, for example, the pH value is not changed.

This is achieved by means of method and means characterized in the claims.

The basis of the development of the method according to the invention, is the known electrolysis of seawater employed on the hulls of ships in order to prevent fouling. By means of electrolysis of a salt water solution, which can be of a physiological type, the active substances NaOCl, $O_3$, free radicals and peroxides are obtained. Such natural decomposition products have a very brief lifetime and must thereafter be produced immediately before utilization. Thereafter they return to their original state or are neutralized such that, immediately subsequent to the treatment, no active substances are present. The substances are, moreover, innocuous to the mucous membrane and connective tissue and are present only in very small amounts. It is thus extremely important that the treating agent does not contain harmful toxic substances and that the active substances are decomposed they can reach the stomach if the agent were to be swallowed. The electrolyzed salt water solution is quite simply sprayed into the mouth and onto the teeth, so that the entire cavity is rinsed out, the solution thereby also penetrating between the teeth and into places inaccessible to a brush. The active substances then act on the primary film by breaking up the adsorbed molecules and loosen the primary film from its base, together with any attached microbes. It is preferably to combine the rinsing or spraying with normal use of a toothbrush in order to dislodge any food residue or the like which has become adhered. Toothpicks and the like can of course also be used for this purpose.

The means according to the invention is preferably effected as an aerosol can or similar pressurized container; however, an embodiment where an electric or manually operated pump is used in place of propellent gas is also possible.

The invention is further explained in the following with reference to a diagrammatic drawing which illustrates two embodiment examples of a means according to the invention.

FIG. 1 illustrates an aerosol can 1 containing a physiological NaCl solution 2 having a pH value of between, for example, 7.2 and 7.8. The aerosol can 1 is provided at the top area thereof with a conventional spray or atomising mechanism 3, the said mechanism, if desired, being provided with a tube or extension 4 for spraying into the oral cavity, and possibly for connection to a toothbrush. In the central portion of the aerosol can, a tube 5 is inserted which extends to adjacent the bottom of the can. In this tube, two electrodes 6, 7 are arranged which are preferably plate-shaped, but may be of any suitable shape and may be spaced, for example, 6–7 mm from each other. At the upper portion of the can 1, two contact points 8, 9 are provided which are connected to the electrodes 6, 7 and to which contact points an electric source of direct current 10 can be connected, for example, a small battery with a voltage of less than 40, preferably 6–15 volt.

The electrodes can of course be arranged in another manner, for example, extending through the bottom of the can, and into the tube 4, whereby they can be directly connected to the battery 10 arranged at the bottom of the can 1.

A propellent gas, for example, aerosol gas 11, is located above the salt water solution.

When the button is pressed, the propellent gas forces the liquid up through the tube 5, the said button connecting, at the same time, the current supply to the electrodes such that electrolysis is initiated. An electrolysis of the small amount of liquid in the tube then takes place, i.e. the liquid is electrolyzed while being forced through the tube and to the spray nozzle. In the first instant, however, immediately afterwards, the electrolysis has carried out a decomposition of the solution, and the active substances which dissolve the primary film are sprayed into the mouth. In this manner, an effective and wholly innocuous treatment of teeth and oral cavity is achieved.

It is of course possible in another embodiment example to utilize an electric pump, which pumps the solution to the spray nozzle, instead of a propellent gas, or manual pumping may also be utilized.

FIG. 2 illustrates a further embodiment example of the means according to the invention where the same reference numbers are used for the same parts as on FIG. 1. In this embodiment the discharge tube or extension member is signified by 12 and comprises a defined compartment 13 wherein the two electrodes 6, 7 are arranged and on the exterior of which the contact points 8, 9 are provided for connection to a source of current 10.

The means operates in the same manner as that illustrated on FIG. 1, with the exception that the compartment 13 must first be filled with liquid prior to initiation of the electrolysis. The current can, in the same manner as on FIG. 1, be connected by pressure on the releaser button for the spray device 3.

This embodiment can also be varied by a dispensing spray, particularly if the spraying is undertaken manually, in that only the amount of liquid located in the compartment 3 being discharged prior to renewed filling of the compartment 13.

This embodiment has the advantage that the container 1 can be replaced when empty, while the electrolysis means is used several times.

Having described my invention, I claim:

1. Apparatus for removing adsorbed film and microorganisms from teeth and the oral cavity comprising a an aerosol can holding a neutral salt water solution, said can being provided with a device for spraying of the solution, means defining a compartment arranged in connection with the spray device so that solution to be sprayed passes through said compartment, said compartment containing two spaced-apart electrodes which, via contact points are connected to a current source so that solution passing through said compartmment is electrolyzed to produce decomposition products.

2. In a hand-held apparatus for spraying a teeth-treating liquid into the human mouth: a container of a size adapted to be held in one hand of an operator for holding a neutral salt water solution; a spray device including a nozzle carried by the container for directing a spray of the solution into the mouth; actuating means operable by the operator's finger while the container is being held for actuating said spray device; means defining a compartment supported by the container and arranged with the container and with the spray device so that solution to be sprayed passes through said compartment; and means for electrolyzing solution passing through said compartment, said means including spaced-apart electrodes arranged within said compartment in a position to be contacted by solution passing therethrough.

3. Apparatus as in claim 2 wherein the container is an aerosol can.

4. Apparatus as in claim 2 including a switch operated by operation of said actuating means to connect said electrodes to an electrical power source.

5. Apparatus as in claim 2 wherein said spray device includes an electrically operated pump.

6. Apparatus as in claim 2 wherein said spray device includes a manually operated pump.

7. Apparatus as in claim 2 wherein said compartment is a tube extending downwardly in the container and having an open lower end adjacent the bottom of the container.

8. Apparatus as in claim 2 wherein said compartment forms part of a spray tube on the spray device.

9. Apparatus as in claim 8 wherein the compartment and spray tube are releasably connected to the container.

* * * * *